United States Patent [19]

Ninomiya et al.

[11] Patent Number: 5,413,792

[45] Date of Patent: May 9, 1995

[54] MUCOADHESIVE POLYSILOXANE PASTE-LIKE BASE AND PREPARATION

[75] Inventors: Hiroshi Ninomiya, Saitama; Yosuke Urabe, Kanagawa, both of Japan

[73] Assignees: Dow Corning K.K.; Nippon Kayaku Kabushiki Kaisha, both of Tokyo, Japan

[21] Appl. No.: 817,257

[22] Filed: Jan. 3, 1992

Related U.S. Application Data

[60] Division of Ser. No. 784,084, Nov. 1, 1991, abandoned, which is a continuation of Ser. No. 498,523, Mar. 26, 1990, abandoned.

[51] Int. Cl.$^6$ .................... A61K 47/34; A61K 47/30; A61K 9/06
[52] U.S. Cl. .................... 424/434; 424/435; 514/772.2; 514/772.3; 514/772.4
[58] Field of Search .............. 524/19; 514/772, 772.2, 514/772.3, 772.4, 772.5, 772.1; 424/434, 435

[56] References Cited

U.S. PATENT DOCUMENTS

| | | | |
|---|---|---|---|
| 3,953,591 | 4/1976 | Snyder | 424/80 |
| 4,059,686 | 11/1977 | Tanaka et al. | 424/19 |
| 4,431,632 | 2/1984 | Burns | 514/772.6 |
| 4,855,129 | 8/1989 | Steinbach | 424/63 |
| 4,894,224 | 1/1990 | Kuwata et al. | 514/772 |
| 4,925,659 | 5/1990 | Grollier et al. | 514/881 |
| 4,946,853 | 8/1990 | Bannon et al. | 514/343 |
| 5,032,384 | 7/1991 | Yeh et al. | 424/435 |

FOREIGN PATENT DOCUMENTS

| | | |
|---|---|---|
| 0289342 | 11/1988 | European Pat. Off. |
| 035301A2 | 7/1989 | European Pat. Off. |
| 2268516 | 4/1976 | France |

OTHER PUBLICATIONS

Henig ". . . Cosmeceutical" Washington Post Jun. 12, 1990.

*Primary Examiner*—Thurman K. Page
*Assistant Examiner*—Peter F. Kulkosky
*Attorney, Agent, or Firm*—Sharon K. Severance

[57] ABSTRACT

The specification describes and claims a paste-like preparation comprising (A) a paste-like base comprising a polyorganosiloxane and a water-soluble polymeric material which are preferably present in a ratio by weight from 3:6 to 6:3 and (B) an active ingredient.

6 Claims, No Drawings

MUCOADHESIVE POLYSILOXANE PASTE-LIKE BASE AND PREPARATION

This is a divisional of application Ser. No. 07/784,084 filed on Nov. 1, 1991, now abandoned, which is a continuation of application Ser. No. 07/498,523 filed on Mar. 26, 1990, now abandoned.

BACKGROUND OF THE INVENTION

The present invention relates to a paste-like base having good local retentivity and to preparations containing such bases and an active ingredient.

Hitherto, a very large number of sticky paste preparations have been designed. For example, an ointment comprising an oily ointment base having sodium polyacrylate kneaded therewith, which is intended to stick to the surface of a wet mucous membrane, is known (see U.S. Pat. No. 4,059,686).

When applied to a mucous membrane, although the polymeric material absorbs water and becomes viscous on the wet surface whereby the stickiness increases with a lapse of time, the local retentivity is not sufficient and degradation of the paste starts within a relatively short period of time so that there is not always obtained a satisfactory result from the standpoint of covering and protection on the membrane.

We have now found that a paste comprising certain polyorganosiloxanes and a water-soluble polymeric material not only strongly sticks to a wet surface but is excellent in retentivity such that it is retained there for a long period of time.

SUMMARY OF THE INVENTION

The present invention provides in one of its aspects a paste-like base comprising a polyorganosiloxane and a water-soluble polymeric material.

The present invention provides in another of its aspects a preparation comprising a paste-like base comprising a polyorganosiloxane and a water-soluble polymeric material, and an active ingredient.

The polyorganosiloxane which is used in the present invention is in the liquid or gum state at room temperature and is preferably one which is mainly linear and which comprises predominantly $R_2SiO$ units wherein the organo group R represents a lower alkyl group, a halogenated alkyl group, an alkenyl group, or an aryl group, and the terminal units of which are $R'R_2SiO_{\frac{1}{2}}$ units in which R is as above and R' is an R group or a hydroxyl group. These substantially linear polydiorganosiloxanes are known and include from a silicone oil having a viscosity of 10 CS or more at 25° C. to a so-called raw rubber having a viscosity of 1,000,000 CS or more at 25° C. In this case, they may contain an $RSiO_{3/2}$ unit or an $SiO_{4/2}$ unit. Further, they may contain fillers of the type which are usually compounded in silicone. Specific examples of liquid polyorganosiloxanes suitable for use in the present invention include Dow Corning Medical Fluid, which is a trimethylsilyl polydimethylsiloxane having a viscosity of 20 to 25,000 cSt, and Dow Corning 556 Fluid which is a polyphenylmethylsiloxane fluid having a viscosity of 20 cSt, and specific examples of polyorganosiloxane gums suitable for use in the present invention include the uncured gum which is employed in Silastic Q7-4535 Medical Grade ETR elastomer namely a dimethylmethylvinylpolysiloxane having a viscosity of about 1,000,000 cSt, with or without the presence of up to 50% by weight of a finely divided fumed silica, in which case the viscosity of the filled gum is of the order of at least 1,000,000 cSt at 25° C.

One may employ from about 3 to 95% by weight, preferably from 10 to 90% by weight and more preferably from 20 to 80% by weight of the polyorganosiloxane based on the weight of the base.

Water-soluble polymeric materials which may be used in the present invention have a viscosity in aqueous solution which is preferably as high as possible. However, even when the viscosity is not so high, if such a water-soluble polymeric material is compounded in a high ratio in the base, it is possible to increase the stickiness. Accordingly, in application to a skin or intraoral mucous membrane, almost all those polymeric materials can be employed which are of acceptable safety, including irritation. More specifically, the following materials can be enumerated.

Examples of water-soluble synthetic polymeric materials include water-soluble acrylic polymeric materials such as carboxyvinyl polymers (such as polyacrylic acid, polymethacrylic acid, and copolymers or partially crosslinked products thereof) and water-soluble salts thereof (such as ammonium salts and alkali metal salts, e.g., sodium salts and potassium salts), and polyacrylamide and copolymers or partially crosslinked products between polyacrylamide and the foregoing carboxyvinyl polymer, with the molecular weight being generally about 20,000 or more and preferably from about 50,000 to 15,000,000; or water-soluble cellulose derivatives (such as methyl celluloses, ethyl celluloses, hydroxymethyl celluloses, hydroxypropyl methyl celluloses, and carboxymethyl celluloses ), carboxymethylchitin, polyvinylpyrrolidone, polyvinyl alcohol, ester gum, water-soluble derivatives of starch (such as hydroxypropyl starch and carboxymethyl starch), and water soluble polyethylene oxides with the average molecular weight being generally from 20,000 to 9,000,000 and preferably from 100,000 to 7,000,000. Examples of natural polymeric materials include hyaluronic acid, sodium alginate, atherocollagen, gelatin, gluten, gum arabic, mannan, dextran, tragacanth, amylopectin, xanthan gum, cholla gum, locust bean gum, casein, pectin, and fibrin glue.

The water-soluble polymeric is preferably a particulate solid at room temperature having a mean particle diameter of from about 0.5 to 200 micrometers and preferably from about 2 to 100 micrometers. A suitable amount of the water-soluble polymeric material is from about 97 to 5% by weight and preferably from about 90 to 10% by weight based on the weight of the base. A suitable ratio of the polydiorganosiloxane to the water-soluble polymeric material is from about 1:9 to 9:1 and preferably from about 3:6 to 6:3 by weight.

If desired, in order to adjust the properties of the base, the paste-like base of the present invention may contain other components (called "paste adjusting components") such as fatty bases or other auxiliary agents. Examples of the fatty bases include petroleum jelly, paraffins, Plastibase 50W, (which is a mixture of 100 parts by weight of liquid paraffin and 5 parts by weight of a polyethylene of molecular weight 21,000), polyethylene glycol, various vegetable fats and oils, various animal fats and oils, waxes, unguentum simplex, hydrophilic vaseline, purified lanolin, dextrin fatty acid esters, fatty acid glycerides, fatty acids, liquid paraffin, squalane, and lanolin alcohol. One may use from 1 to about 70% by weight and preferably from about 5 to 50% by weight of these paste adjusting components based on the weight of the base.

By adding an active ingredient to the paste-like base of the present invention, a paste-like preparation having good local retentivity, particularly local retentivity in a wet part can be obtained. As the active ingredient, there are no particular restrictions, and examples include active ingredients for drug, quasi-drug, cosmetic, perfume, antiseptic, or fertilizer. Examples of main active ingredients for drug include a germicidal component, an antibiotic component, a chemotherapeutic component for cancer, a local anaesthetic component, an antiphlogistic analgesic component, an antiphlogistic enzyme, a vasodilator component, an antitussive expectorant, an antianginal component, a hemostatic component, a hormone, a gastrointestinal component, an antidiabetic component, and a contraceptive component.

A suitable proportion of the respective components in the paste-like preparation is frown about 3 to 95% and preferably from about 10 to 90% by weight of polydiorganosiloxane, from about 97 to 5% and preferably from about 90 to 10% by weight of the water-soluble polymeric material, and not higher than about 30%, preferably not higher than about 20% and more preferably not higher than 15% by weight of the active ingredient, respectively. The lower limit of the active ingredient is not particularly limited so long as the desired pharmacological activity is realized and may be, for example, about 0.005% by weight of the preparation, and, depending upon the type of the active ingredient, is preferably about 0.01% by weight of the preparation.

The paste-like preparation may further comprise the above-described paste adjusting components, taste correctives, odor correctives, colorants, and the like. A suitable proportion of the paste adjusting components is up to about 70% by weight based on the whole of the preparation.

In order to produce the paste-like base or paste-like preparation of the present invention, the respective components of the base or preparation and, if desired, the paste adjusting components, taste correctives, odor correctives, colorants, and the like are uniformly mixed in any order from 0° C. to 50° C. and preferably from 5° C. to 30° C. As the mixing method, for example, a method in which, using a rotary screw-equipped kneader or a mixer equipped with baffles and stirring blades, the respective components are uniformly mixed at a stirring rate of form about 10 to 200 rpm while undergoing defoaming under a reduced pressure of 30 mmHg or lower can be employed.

The paste-like preparation can also be obtained by uniformly mixing the active ingredient with the above-described paste-like base.

The paste-like preparation of the present invention can be used by applying to a skin or a mucous membrane. Further, the paste-like preparation can be used as a preparation for oral administration or a suppository upon being filled in, e.g., a capsule. During retention of the preparation on a surface, the active ingredient is progressively released from the preparation.

DETAILED DESCRIPTION

There now follows a description of Examples selected to enable a better understanding of the invention.

EXAMPLE 1

Retentivity test using a beaker:

A paste for use in a preparation according to the invention but containing a dye as active ingredient, was made by mixing the ingredients of the following formulation.

| Polydimethylsiloxane (PDMS): | 48 g |
|---|---|
| Viscosity: 1000 cs | |
| Sodium polyacrylate (PANA): | 48 g |
| Average molecular weight (M): 3,600,000 | |
| Mean particle diameter (R): 3.6 microns | |
| Plastibase ® 50 W: | 3.95 g |
| Methylene blue: | 0.05 g |
| Total: | 100 g |

An ointment having the following formulation was used as a control sample.

| Sodium polyacrylate (PANA): | 30 g |
|---|---|
| Average molecular weight (M): 3,600,000 | |
| Mean particle diameter (R): 15.1 microns | |
| Plastibase ® 50 W: | 69.95 g |
| Methylene blue: | 0.05 g |
| Total: | 100 g |

To a dry inner wall of a 500 ml beaker was uniformly applied 1 g of each sample in an area of $1 \times 2$ cm$^2$ and in a thickness of about 0.5 cm. 500 ml of distilled water was then poured into the beaker at 37° C. for impregnation and quickly stirred at 600 rpm. After 4 hours, the paste attached to the beaker wall was collected, and the proportion of the remaining dye (methylene blue) contained therein was measured. Further, the state (appearance) of the paste attached to the wall was observed. The results are shown in Table 1.

TABLE 1

| Sample | Remaining Dye % by Weight | State (Appearance) of Paste |
|---|---|---|
| Product of Invention | 86.2 | The outside of the paste absorbed water to swell and became about twice in thickness. The center portion did not alter. |
| Control Product | 24.2 | The attached area did not alter, and the thickness decreased to 1/3 or less. |

As is clear from the above Table 1, it can be understood that with respect to the control paste, the thickness became ⅓ or less, whereby the retentive amount on the attached part was small. This is supported by the fact that the amount of the remaining dye was greatly reduced to about 24%. On the other hand, with respect to the paste of the present invention, the attached area did not decrease, and the paste had swollen twice or more in terms of thickness. Further, the amount of the remaining dye was about 86%. Thus, it can be understood that the paste is excellent in retentivity in the attached part.

EXAMPLE 2

Intraoral retentivity test:
(Sample)
Samples having the formulations as shown in Table 2 were used.
(Experimental Method)
0.3 g of each of the samples was applied to a wet intraoral mucous membrane surface on the inside of the lower lip, which had been well wetted with saliva. After six hours, the sample attached to the mucous membrane surface was collected, and the proportion of the remaining dye contained therein was measured. (If the proportion was higher than that in Example 1, the amount of the remaining paste was high, whereas if the proportion was low, the amount of the remaining paste was low. Thus, this proportion was used as an index for the retentivity.) The results are shown in Table 2.

TABLE 2

| Sample | Components and Composition [viscosity (CS), M (molecular weight) (ten thousand)/R (mean particle diameter) (microns)] | Remaining Dye (W/W %) |
| --- | --- | --- |
| Product 1 of Invention | PDMS (viscosity: 1000 CS): 48 g, PANA (M: 360/R: 8.6): 48 g, Plastibase 50 W: 3.95 g | 79.0 |
| Product 2 of Invention | PDMS (viscosity: 12500 CS): 30 g, PANA (M: 480/R: 10.5): 30 g, white vaseline: 39.9 g | 79.0 |
| Product 3 of Invention | PDMS (viscosity: 500 CS): 11 g, polyacrylamide (M: 15/R: 29.8): 84 g, squalane: 4.95 g | 60.7 |
| Product 4 of Invention | PDMS (viscosity: 3000 CS): 21 g, gelatin (R: 18.5): 15 g, PANA (M: 900/R: 10): 50 g, lanolin: 13.95 g | 59.1 |
| Product 5 of Invention | PDMS (viscosity: 5000 CS): 20 g, methyl cellulose (M: 40): 31 g, xanthan gum: 34 g Plastibase 50 W: 11.95 g | 72.4 |
| Product 6 of Invention | PDMS (viscosity: 5000 CS): 50 g, PANA (M: 480/R: 10.5): 49.95 g | 76.0 |
| Product 7 of Invention | PDMS (viscosity: 30000 CS): 30 g, polyethylene oxide (M: 5/R: 65): 30 g, gelatin: 14.95 g | 55.4 |
| Product 8 of Invention | PDMS (viscosity: 30000 CS): 30 g, polyethylene oxide (M: 5/R: 65): 55 g, white vaseline: 14.95 g | 49.7 |
| Product 9 of Invention | PDMS (viscosity: 3000 CS): 25 g, polyethylene oxide (M: 80/R: 16.1): 60 g, stearic acid monoglyceride: 14.95 g | 66.2 |
| Product 10 of Invention | PDMS (viscosity: 300000 CS): 30 g, PANA (M: 480/R: 10.5): 20 g, white vaseline: 50 g | 42.8 |
| Comparative Example 1 | PANA (M: 360/R: 15.1): 30 g, Plastibase 50 W: 69.95 g | 19.5 |

CS: centistoke, PDMS & PANA: same as described above

As is clear from the above table, the proportion of the remaining dye in the products of the present invention is twice or more as compared with the control product. Thus, it can be understood that the products of the present invention are excellent in intraoral rententivity.

EXAMPLE 3

A preparation according to the present invention comprising 50 parts of PDMS having a viscosity of 12500 CS, 45 parts of a fibril glue powder, and 5 parts of fradiomycin sulfate was applied to a cut on a human finger.

A sticky gel membrane was formed on the cut due to the contact between an oozed liquid and blood, and the blood-flow was quickly stopped, good encrustation was observed, whereby cure of the cut was acclerated.

From the foregoing results, the preparation of the present invention sticks well to wet surfaces and remains coherent, and can be expected to exhibit a protective effect against an ulcer surface, etc.

EXAMPLE 4

48 g of PDMS having a viscosity of 1000 CS, 48 g of PANA having an average molecular weight of 3,600,000 and a mean particle diameter of 8.6 microns, and 3.95 parts of Plastibase 50W were charged into a kneader and uniformly kneaded at 75 rpm for about one hour while reducing the pressure in the kneader to 15 mmHg at room temperature of from 20° to 25° C., to obtain a paste-like base according to the invention.

EXAMPLE 5

30 g of PDMS having a viscosity of 12500 CS, 30 g of PANA having an average molecular weight of 4,800,000 and a mean particle diameter of 10.5 microns, 39.95 g of white vaseline, and 0.05 g of pleomycin sulfate were charged into a kneader and uniformly kneaded to 50 rpm for about two hours while reducing the pressure at 20 mmHg at room temperature of from 15° to 20° C., to obtain a paste-like preparation according to the present invention.

What is claimed is:

1. A non-aqueous mucoadhesive base comprising
   (i) 3 to 95 weight percent of a polyorganosiloxane, wherein the polyorganosiloxane is comprised predominantly of $R_2SiO$ units and has chain terminating units $R'R_2SiO_{\frac{1}{2}}$ where each R represents a lower alkyl group, a halogenated alkyl group, an alkenyl group or an aryl group and each R' represents a group R or a hydroxyl group, and the polyorganosiloxane is liquid or a gum at 25° C.; and
   (ii) 5 to 97 weight percent of a water-soluble polymeric material selected from the group consisting of water soluble polymers and copolymers of acrylic acid, methacrylic acid, acrylamide, cellulose derivatives and salts thereof, carboxymethylchitin, polyvinylpyrrolidone, polyvinyl alcohol, starch derivatives, polyethylene oxide, gelatin, collagen and natural gums; the weight percent being based on the sum of (i) and (ii) and wherein the polysiloxane and water soluble polymeric material are present in a ratio by weight of from 1:9 to 9:1 and wherein the base is capable of adhering to a wet surface.

2. A base according to claim 1 wherein the water-soluble polymeric material is a particulate solid, the particles of which have a mean diameter of 0.5 to 200 micrometers.

3. A base according to claim 2 wherein the particles have a mean diameter of 2 to 100 micrometers.

4. A base according to claim 1 wherein the water-soluble polymeric material provides 10 to 90 % by weight of the base.

5. A base according to claim 1 wherein the polyorganosiloxane and water-soluble polymeric material are present in a ratio by weight from 3:6 to 6:3.

6. A base according to claim 1 also comprising up to 70% by weight based on the weight of (i) and (ii) of a paste adjusting component chosen from fatty materials.

* * * * *